(12) United States Patent
Park et al.

(10) Patent No.: US 11,938,232 B2
(45) Date of Patent: Mar. 26, 2024

(54) X-RAY IRRADIATOR FOR SINGLE BLOOD BAGS

(71) Applicant: KOREA INSTITUTE OF RADIOLOGICAL & MEDICAL SCIENCES, Seoul (KR)

(72) Inventors: Seung Woo Park, Seoul (KR); Mun Sik Choi, Uijeongbu-si (KR); Su Chul Han, Seoul (KR); Jong Hyun Back, Changwon-si (KR)

(73) Assignee: KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 473 days.

(21) Appl. No.: 17/414,295

(22) PCT Filed: Dec. 17, 2019

(86) PCT No.: PCT/KR2019/017883
§ 371 (c)(1),
(2) Date: Jun. 15, 2021

(87) PCT Pub. No.: WO2020/130574
PCT Pub. Date: Jun. 25, 2020

(65) Prior Publication Data
US 2022/0062451 A1    Mar. 3, 2022

(30) Foreign Application Priority Data
Dec. 19, 2018  (KR) .......................... 10-2018-0165396

(51) Int. Cl.
*A61L 2/08*   (2006.01)
*A61L 2/00*   (2006.01)
*A61M 1/02*   (2006.01)

(52) U.S. Cl.
CPC ......... *A61L 2/0041* (2013.01); *A61M 1/0286* (2014.02); *A61L 2202/122* (2013.01); *A61L 2202/22* (2013.01)

(58) Field of Classification Search
CPC ........................... A61L 2/0041; A61L 2202/22
See application file for complete search history.

(56) References Cited

U.S. PATENT DOCUMENTS

| | | | | |
|---|---|---|---|---|
| 4,296,068 A | * | 10/1981 | Hoshino | ............. B05B 13/0264 422/62 |
| 2003/0035751 A1 | * | 2/2003 | Hanley | ..................... A61L 2/10 422/24 |

(Continued)

FOREIGN PATENT DOCUMENTS

| | | |
|---|---|---|
| CN | 102320397 A | 1/2012 |
| CN | 102861104 A | 1/2013 |

(Continued)

OTHER PUBLICATIONS

The Extended European Search Report for European Patent Application No. 19900036.5, dated Aug. 5, 2022.

*Primary Examiner* — Donald R Spamer

(57) ABSTRACT

The present invention relates to an X-ray irradiator for single blood bags, comprising: an X-ray irradiator main body provided with a chamber configured to safely hold a single blood bag therein and an X-ray tube configured to irradiate the chamber with X-rays; a loading part configured to load the blood bag; and a transfer part configured to transfer the blood bag between the loading part and the chamber to which X-rays are to be emitted. The X-ray irradiator for single blood bags according to the present invention can treat a single blood bag with X-rays, such that treatment optimized for a small amount of a blood bag can be performed, and a system configuration can be simplified by using an X-ray tube.

15 Claims, 20 Drawing Sheets

(56) References Cited

U.S. PATENT DOCUMENTS

| | | |
|---|---|---|
| 2013/0177136 A1 | 7/2013 | Moses |
| 2014/0250943 A1* | 9/2014 | Pericolini ............. F25D 25/027 |
| | | 62/441 |
| 2018/0078665 A1* | 3/2018 | Buccellato ........... B65D 75/305 |

FOREIGN PATENT DOCUMENTS

| | | |
|---|---|---|
| CN | 104040273 A | 9/2014 |
| CN | 106620910 A | 5/2017 |
| JP | H067410 A | 1/1994 |
| JP | H06205818 A | 7/1994 |
| JP | H07-282518 A | 10/1995 |
| JP | H1043275 A | 2/1998 |
| JP | 2000-262595 A | 9/2000 |
| JP | 2017146109 A | 8/2017 |

* cited by examiner

X-RAY IRRADIATOR FOR SINGLE BLOOD BAGS

The research related to the present invention was carried out by a project (Project No.: 1711076687) conducted with the support of the National Research Foundation of Korea with the funding of the government (Ministry of Science and ICT).

TECHNICAL FIELD

The present disclosure relates to an X-ray irradiator for single blood bags, and more particularly, to an X-ray irradiator for single blood bags capable of performing X-ray irradiation treatment of the blood bags one by one.

BACKGROUND ART

A blood bag for transfusion is configured to accommodate a certain amount of blood, and is stored at low temperatures and used if necessary. Since blood for transfusion contains part of the donor's immune system, it is necessary to neutralize the immune system in order to receive a blood transfusion.

Specifically, when lymphocytes contained in the blood are not removed before transfusion, the transfused lymphocytes proliferate in the patient's body with a weakened immune function, which may cause a graft versus host disease (GVHD) that attacks the patient's epithelial cells. Accordingly, a general method of performing irradiation with radiation to remove lymphocytes present in blood for transfusion is performed by using a blood irradiation device, and Cs-137 is mainly used as a gamma source. The irradiation is performed with radiation (gamma rays) of about 2,500 rad, and in this case, it is possible to incapacitate only lymphocytes without affecting the function of red blood cells or platelets.

On the other hand, GVHD may be induced even in patients with normal immune function. When tissues in the donated blood are transfused into a patient's body, it does not matter if the tissues in the patient's body are the same as those in the donated blood, but if the tissues are different, lymphocytes may proliferate and attack them. Therefore, even if transfusions are conducted between genetically close relatives, that is, between immediate family members, blood irradiation has to be performed before transfusion.

In this regard, in the related art, radiation is mainly used for the treatment of blood bags, and since ancillary equipment has to be essentially provided for the use of radiation, there is a problem of operational inefficiency in that the equipment becomes complicated and excessively large equipment is used to treat a small number of blood bags.

DISCLOSURE

Technical Problem

An object of the present disclosure is to provide an X-ray irradiator for single blood bags capable of solving the problem of the X-ray irradiator in the related art for treating the blood bags described above.

Technical Solution

According to an aspect of the present disclosure, there is provided an X-ray irradiator for single blood bags comprising a main body of an X-ray irradiation unit provided with a chamber configured to safely hold a single blood bag therein and an X-ray tube configured to irradiate the chamber with X-rays, a loading part configured to load the blood bag, and a transfer part configured to transfer the blood bag between the loading part and the chamber to which X-rays are to be emitted.

Here, the loading part may include a tray slot configured to load with a plurality of trays, and the tray may be configured to individually load the blood bag.

Meanwhile, the transfer part may be configured to transfer the tray in a state in which the blood bag is held onto the tray.

Furthermore, the transfer part may be configured to reciprocate the tray between a first position for exchanging the tray with the loading part and a second position for exchanging the tray with the chamber.

Furthermore, the X-ray irradiator for single blood bags may further include a shielding door configured to shield the blood bag from the outside when the blood bag is disposed at an X-ray irradiation position in the chamber.

Meanwhile, the X-ray irradiator for single blood bags may further include a stamping unit provided on a reciprocating path of the transfer part, and configured to make a completion mark on the blood bag transferred after X-ray irradiation is completed in the chamber.

Here, the stamping unit may be provided inside the main body of the X-ray irradiation unit, and may be configured to perform stamping by moving downward and contacting an upper surface of the blood bag.

Meanwhile, the loading part may further include a housing, and the tray slot may be provided inside the housing and configured so that a plurality of the trays are loaded in a vertical direction.

Furthermore, the tray slot may include a plurality of supports spaced apart from each other in a vertical direction to support the plurality of trays, respectively.

Meanwhile, the loading part may further include a hand unit configured to pick up any one tray loaded in the tray slot and move the picked up tray to the first position.

Furthermore, the hand unit may further include a sensor unit configured to determine a relative position of the blood bag on the tray when the tray is picked up, and may be controlled not to draw the tray out from the tray slot when it is determined that a loading position of the blood bag is defective.

Furthermore, the sensor unit of the hand unit may include a plurality of sensors, and the sensors may be provided facing from top to bottom of the tray and determine a position of the blood bag based on values measured by sensors provided in regions adjacent to edges of the tray and in a region adjacent to a central portion thereof.

Meanwhile, the X-ray irradiator for single blood bags may further include a controller configured to control the main body of the X-ray irradiation unit and the loading part, in which the controller is configured to record data on whether X-ray irradiation is completed on the blood bag loaded in the loading part, or whether the loading position is defective.

Meanwhile, the loading part may be further provided with a rotating frame configured to be rotated and include a plurality of tray slots formed to extend radially, and the rotating frame may be configured to locate each of the tray slots to the first position as the rotating frame is rotated.

Meanwhile, the tray slot may further include a holder configured to prevent the tray loaded in the tray slot from being separated.

Meanwhile, the tray slot may further include a tray door configured to prevent the blood bag from being separated.

Advantageous Effects

The X-ray irradiator for single blood bags according to the present disclosure may perform X-ray treatment on single blood bags, which may perform an optimized treatment for a small amount of a blood bag and may simplify a system configuration by using an X-ray tube.

In addition, since a loading part is provided, the number of blood bags desired by a user may be automatically treated with the X-ray, which may increase the degree of freedom of operation.

MODE FOR DISCLOSURE

Figure 1:
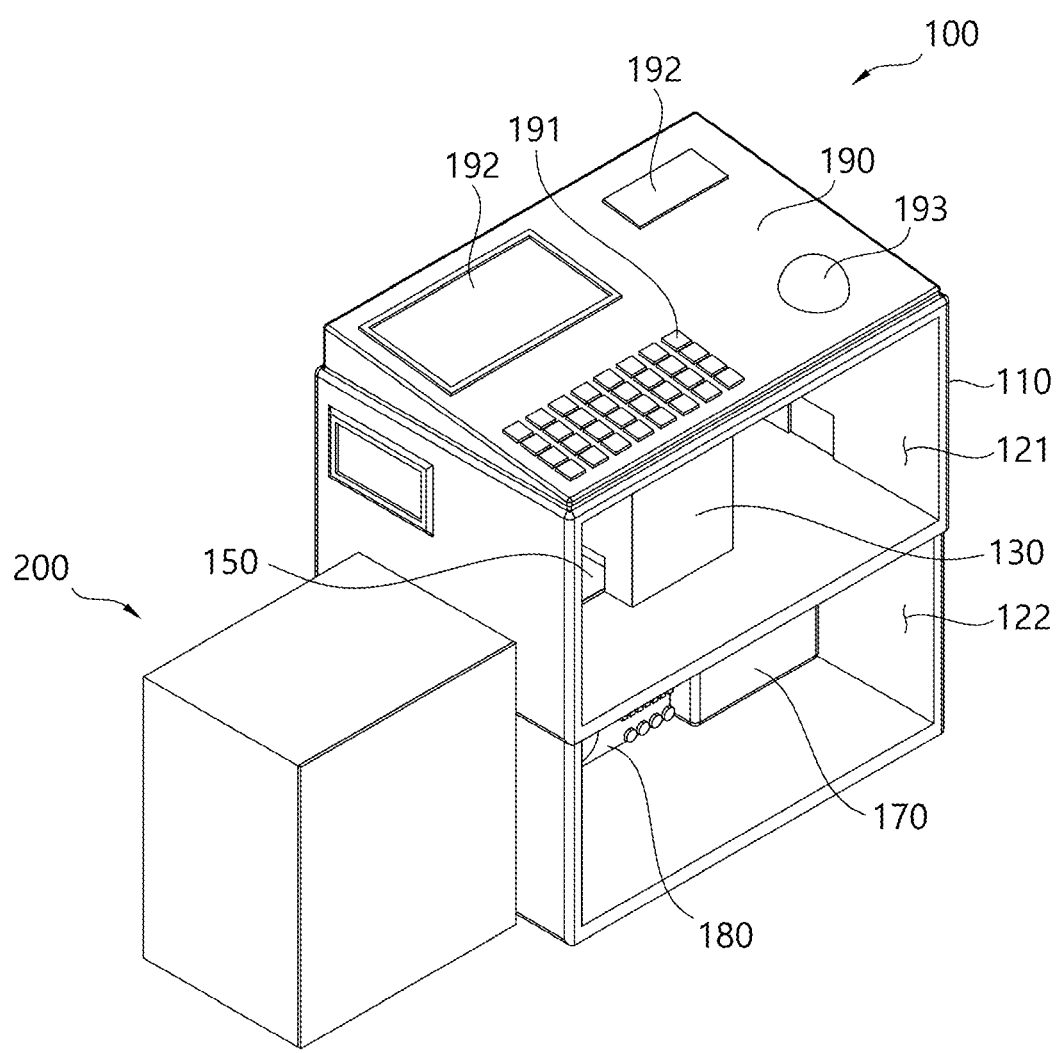
FIG. 1 is a perspective view illustrating a concept of an X-ray irradiator for single blood bags according to the present disclosure.

Hereinafter, an X-ray irradiator for single blood bag according to an embodiment of the present disclosure will be described in detail with reference to the accompanying drawings. In the description of the following embodiments, the names of respective components may be referred to as different names in the art. However, if they have functional similarities and identities, they may be viewed as having a uniform configuration even if a modified embodiment is employed. In addition, symbols added to each component are described for convenience of description. However, the details illustrated on the drawings in which these symbols are indicated do not limit each component to the range within the drawings. Likewise, even if an embodiment in which the configuration in the drawings is partially modified is employed, the embodiment may be regarded as having an equivalent configuration if it has a functional similarity and identity. In addition, when a component is recognized as a component that should be included in view of the level of those of ordinary skill in the art, a description thereof will be omitted.

Hereinafter, an X-ray irradiator for single blood bags according to the present invention will be described in detail with reference to FIGS. 1 to 4d.

Figure 2:
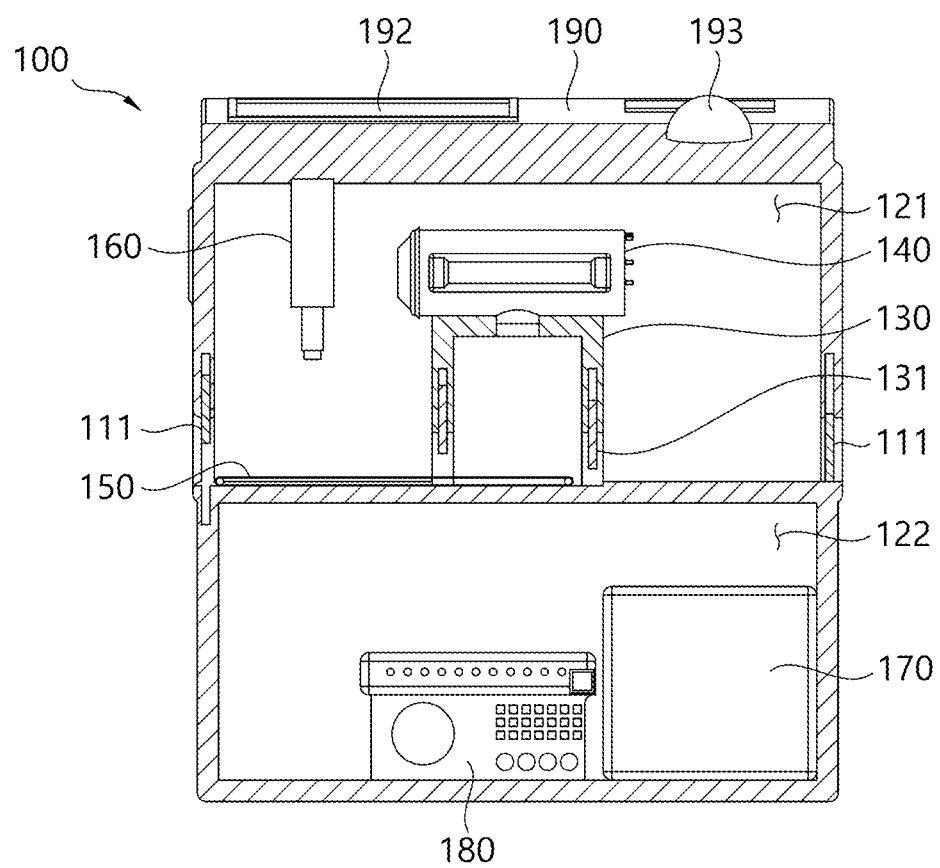
FIG. 2 is a cross-sectional view of the main body of the X-ray irradiator.

FIG. 1 is a perspective view illustrating a concept of an X-ray irradiator for single blood bags according to the present disclosure. In this drawing, the front surface of the housing of the main body of the X-ray irradiator is omitted for convenience of description. FIG. 2 is a cross-sectional view of the main body of the X-ray irradiator.

As shown, the X-ray irradiator for single blood bags 2 according to the present disclosure may be configured to include a main body 100 of an X-ray irradiation unit 140, a loading part 200, and a transfer part 150.

The main body 100 of the X-ray irradiation unit 140 is configured to perform X-ray irradiation for treating the blood bags 2 on the individual basis. The loading part 200 is loaded with a plurality of blood bags 2, and each of the blood bags 2 is configured to be loaded in each of spaces separated from each other so as to aid in transport one by one. The transfer part 150 is configured to transfer the blood bag 2 from the loading part 200 to the main body 100 of the X-ray irradiation unit 140 to supply the blood bag 2 that needs X-ray treatment, or, conversely, to transfer the blood bag 2 on which the X-ray treatment has been completed from the main body 100 of the X-ray irradiation unit 140 to the loading part 200. In the present embodiment, a description will be made on the premise that the transfer part 150 is provided on the main body 100 of the X-ray irradiation unit 140. However, the transfer part 150 may be provided on the main body 100 of the X-ray irradiation unit 140, and may be applied by modifying the configuration so as to be provided on the loading part 200.

The main body 100 of the X-ray irradiation unit 140 may be configured to include a housing 110, a chamber 130, the transfer part 150, the X-ray irradiation unit 140, a control panel 190, a display unit 192, a stamping unit 160, a controller 170, and a power supply unit 180.

The housing 110 is configured to form the overall appearance of the main body 100 of the X-ray irradiation unit 140. The housing 110 may be provided in a hexahedral shape as a whole, and may be divided into an upper stage 121 and a lower stage 122. The upper stage 121 may be a space in which the blood bag 2 is treated, and the lower stage 122 may include a power supply unit 180, a cooler, and the controller 170 for driving the entire device. The housing 110 may further include an outer door configured to move the tray 1 on a side wall thereof. The opening and closing operation of the outer door 111 may be controlled door so that the tray 1 may be transferred between a withdrawal part of the loading part 200 to be described later and the transfer part 150. Meanwhile, the outer door 111 may be provided on both side walls and configured to receive the blood bag 2 from each loading part 200 or such that the user directly supplies the blood bag 2.

Figure 3:
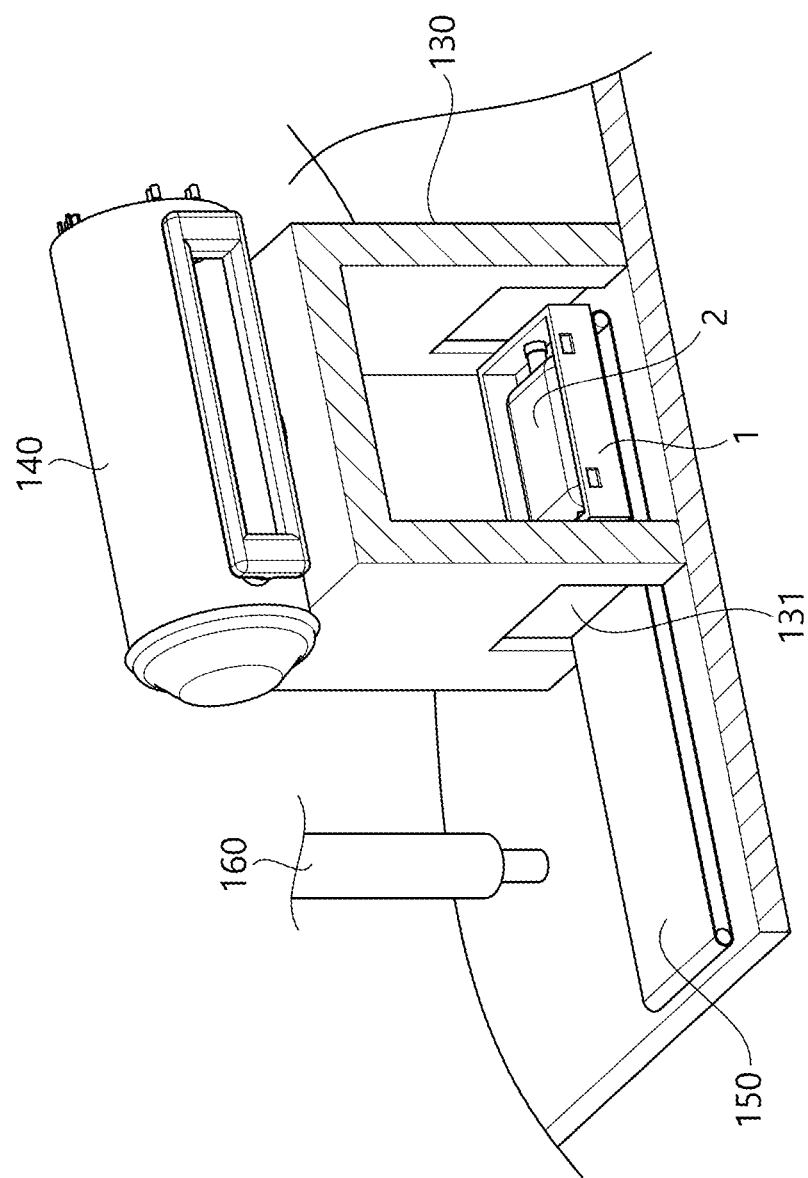
FIG. 3 is an enlarged partial perspective view of a chamber of FIG. 1.

FIG. 3 is an enlarged partial perspective view of the chamber 130 of FIG. 1.

The chamber 130 is a place where X-rays are irradiated in a state in which the blood bag 2 is transferred. The chamber 130 is configured in a size sufficient to allow a single blood bag 2 to be irradiated with X-rays. In this case, one blood bag 2 is transferred to the inside of the chamber 130 in a state of being loaded on one tray 1, and the size of the chamber 130 is determined so that the tray 1 is able to be positioned inside the chamber 130. The height of the upper surface of the chamber 130 may be determined so that when X-ray irradiation is performed from the X-ray irradiation unit 140 toward the blood bag 2 below, which is to be described later, the blood bag 2 may be irradiated with a uniform dose. The chamber 130 may be made of an X-ray shielding material and have a thickness capable of shielding X-rays so that when X-ray irradiation is performed, radiation to the outside is prevented. For example, the chamber 130 may be made of a metallic material and configured to shield X-rays. The chamber 130 may have an opening in the side thereof so that the tray 1 may be transferred from the transfer part. A shielding door 131 may be provided in the opening, and the chamber 130 may be configured to be sealed by closing the shielding door 131 before irradiating the tray 1 with X-rays.

The transfer part 150 is configured to transfer the tray 1 in which the blood bag 2 is loaded. The transfer part 150 may be configured to be horizontally movable in a state of supporting the tray 1, and for example, may be a conveyor belt. One side of the transfer part 150 may be adjacent to the outer door 111, and the other side may be formed to extend to the inside of the chamber 130 by passing through the shielding door 131 of the chamber 130. The transfer part 150 is operated by a control signal from the controller 170, and may be configured such that the tray may be transferred between a first position P1 for exchanging the tray 1 with the loading part 200 and a second position P2 inside the chamber 130 where the tray 1 is subjected to the X-ray treatment.

However, in the present embodiment, a configuration in which the transfer part 150 is a conveyor belt is disclosed, but this is only an example and may be modified into various configurations capable of horizontally moving the tray 1 when applied. In addition, a configuration in which the other side of the transfer part 150 extends to the inside of the chamber 130 is shown, but a separate drive unit may be provided to transfer the tray 1 from the transfer part 150 to the inside of the chamber 130.

The X-ray irradiation unit 140 may be configured to emit X-rays into the chamber 130. The X-ray irradiation unit 140 is provided on the upper side of the chamber 130 to emit X-rays downward, and the X-ray irradiation paths may be formed in the shape of a cone in which an irradiation area is gradually widened toward the lower side. The X-ray irradiation unit 140 may be configured such that an area of X-rays with which the blood bag 2 is irradiated is larger than that of the blood bag 2. That is, the irradiation region of X-rays with which the tray 1 is irradiated may be larger than the cross-sectional area of the blood bag 2. In the case of such a configuration, even if the posture of the blood bag 2 is not changed or the direction of X-ray irradiation is not changed, the X-ray treatment may be uniformly performed as a whole. Meanwhile, the X-ray irradiation unit 140 may be an X-ray tube, for example. The X-ray tube may be configured to include a glass tube, a cathode, an anode, and a target, but since a widely used configuration may be applied, a detailed description thereof will be omitted.

Referring back to FIG. 1, the control panel 190 is provided on the upper surface of the housing 110. The control panel 190 may be configured to allow a user to perform an operation input or display information about state with respect to the main body 100 of the X-ray irradiation unit 140 and the loading part 200 to be described later. The control panel 190 may be provided on the upper surface of the housing 110 in order to improve the operability and recognition of the user, and may be configured to have a slightly tilted inclination toward the front. Accordingly, the user may manipulate the control panel 190 while looking from the top to the bottom, thereby improving convenience.

The control panel 190 may include an input unit 191, a display unit 192, and a notification unit 193.

The input unit 191 may be configured to generate an input signal for the overall operation of the main body 100 of the X-ray irradiation unit 140 and the operation of the loading part 200 with an input of the user.

The display unit 192 is provided on a part of the upper surface of the housing 110. The display unit 192 is configured to receive a signal from the controller 170, which will be described later, and to generate an image signal so that the user may visually recognize the signal. The display unit 192 may be configured to display information on a current progress status, the number of loaded blood bags 2, the number of treated blood bags 2, the type of blood loaded in the blood bag 2, or the like. Meanwhile, since the configuration of images displayed on the display unit 192 may be applied in various configuration methods, further detailed description thereof will be omitted.

The notification unit 193 is configured to notify the user while the X-ray is being emitted, and may induce the user not to approach the main body 100 of the X-ray irradiation unit 140 by making the user aware that X-ray irradiation is in progress.

The stamping unit 160 is configured to perform completion mark stamping on the blood bag 2 on which X-ray irradiation has been completed. The stamping unit 160 may be provided on the upper stage 121 of the housing 110 and may be provided above the transfer part 150. The stamping unit 160 is connected to the upper side of the upper stage, may be formed to extend from top to bottom, and may be raised and lowered in the vertical direction. The stamping unit 160 may be provided with an actuator (not shown) extending in the vertical direction so that the lower end thereof descends to the upper surface of the blood bag 2 to contact the surface of the blood bag 2. The stamping unit 160 may be configured to make a mark on the blood bag 2 using ink. Meanwhile, the stamping unit 160 may be controlled to perform stamping by descending when the transfer part 150 is temporarily stopped at a third position P3 where stamping is performed while transferring the tray 1 from the chamber 130 to the second position P2.

The controller 170 may be configured to perform overall control of the X-ray irradiator. The controller 170 may be provided on the lower station. The main function of the controller 170 may be to control elements for movement of the blood bag 2 and generation of X-rays, and, specifically, may be to control electrical elements such as an X-ray tube, a high voltage generator, and a transformer. In addition, feedback control may be performed by receiving information on the blood bag 2 to be treated using a plurality of sensors.

The power supply unit 180 may be configured to supply power required for electrical elements and mechanical driving elements such as the controller 170, a transformer (not shown), and a high voltage supply (not shown). Since the configuration of the power supply unit 180 may be variously modified into generally available components, a detailed description thereof will be omitted.

Hereinafter, operations in the main body 100 of the X-ray irradiation unit 140 will be described with reference to FIGS. 4a, 4b, 4c, and 4d.

FIGS. 4a, 4b, 4c, and 4d are operational state diagrams illustrating a concept of a process of treating the blood bags 2.

Figure 4A:
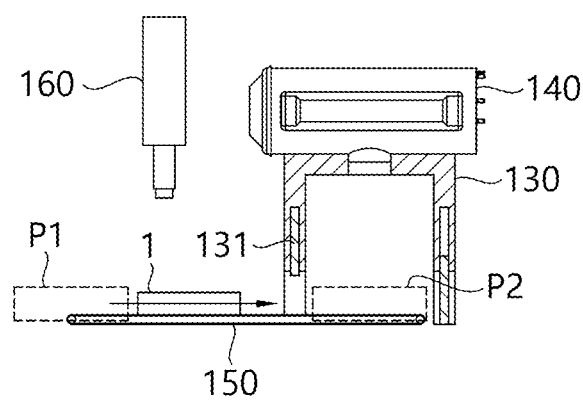
FIGS. 4a, 4b, 4c, and 4d are operational state diagrams illustrating a concept of a process of treating blood bags.
Figure 4B:
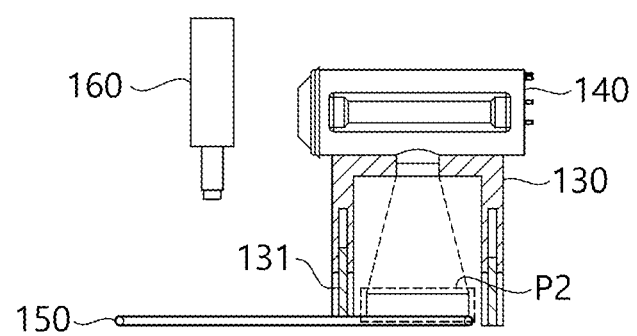

As shown in FIG. 4a, the transfer part 150 is driven, and then the tray 1 is transferred from the first position P1 to the second position P2 inside the chamber 130. That is, according to the configuration of FIG. 4, the tray 1 may be moved from left to right in FIG. 4a. At this time, when the tray 1 is transferred into the chamber 130, the shielding door 131 of the chamber 130 may be raised and opened, and after the tray 1 passes, the shielding door 131 may be closed. Then, as shown in FIG. 4b, the blood bag 2 is irradiated with the X-rays generated by the X-ray irradiation unit 140. The X-ray irradiation time may vary depending on factors such as the size of the blood bag 2, the type of blood contained in the blood bag 2, for example, a plasma component and a whole blood component. In the case of whole blood, X-rays may be emitted for 5 to 10 minutes depending on the strength of the X-rays.

Figure 4C:
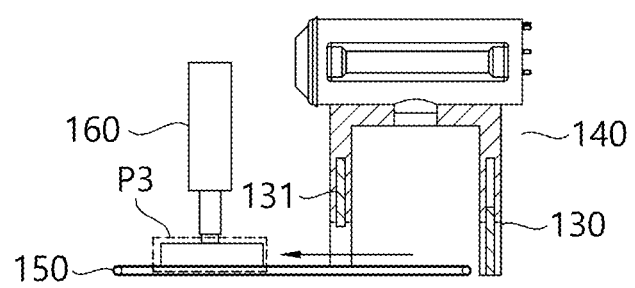

Then, as shown in FIG. 4c, when the X-ray irradiation is completed, the shielding door 131 is opened again and the transfer part 150 is operated to remove the tray 1 from the chamber 130, and the transfer part 150 is controlled to be temporarily stopped at the third position P3, which is determined to be on the lower side of the stamping unit 160. Then, by operating the stamping unit 160, stamping is performed on the outer surface of the blood bag 2 loaded on the tray 1 to indicate that the X-ray treatment is complete.

Figure 4D:
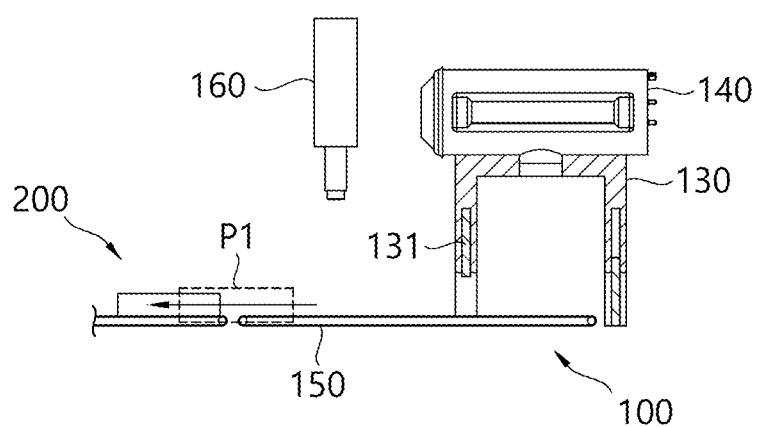

After the stamping is completed, as shown in FIG. 4d, by operating the transfer part 150, the tray 1 is moved to the first position P1, and in the first position P1, the loading part 200 to be described later transfers and loads the tray 1.

Hereinafter, the loading part 200 will be described in detail with reference to FIGS. 5 to 9.

Figure 5:
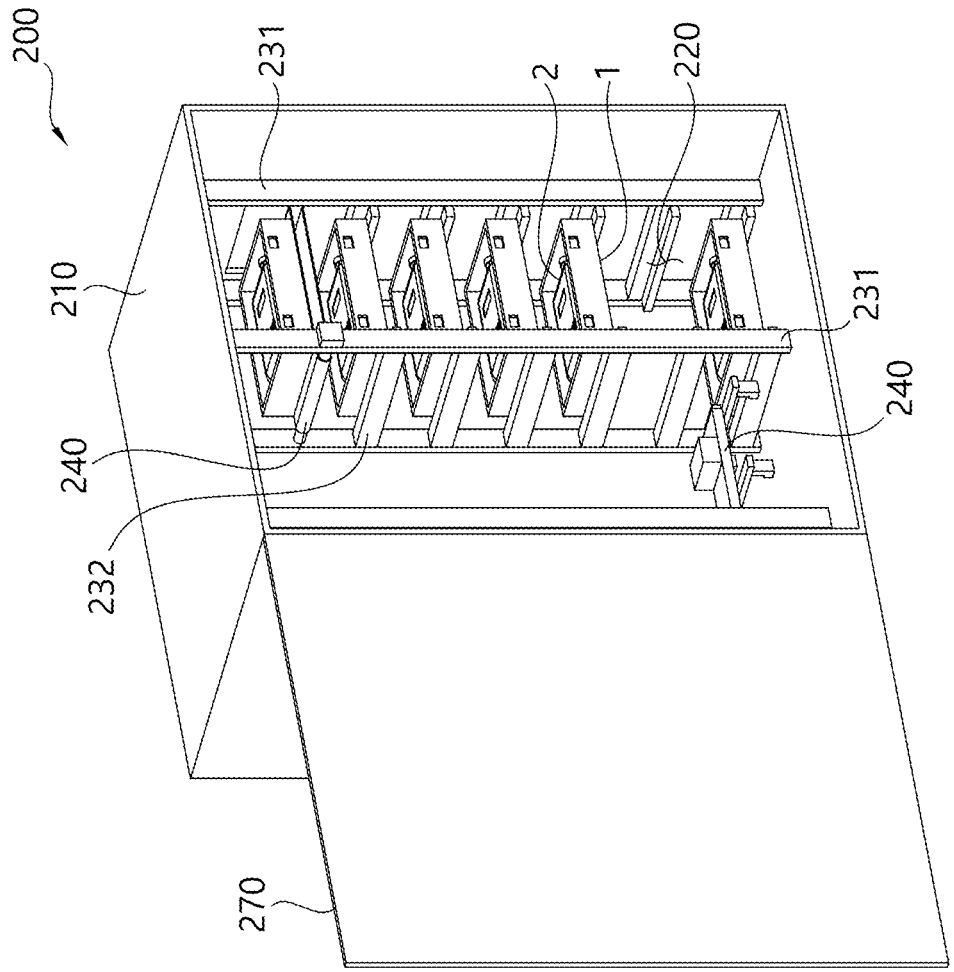
FIG. 5 is a perspective view of a loading part.

FIG. 5 is a perspective view of the loading part 200. As shown, the loading part 200 is configured to be loaded with a plurality of trays 1 to individually supply each of the trays 1 to the main body 100 of the X-ray irradiation unit 140 or load the tray 1 in a loading slot. The loading part 200 may be configured to include a case 210, a tray slot 220, a hand unit 250, a temperature control unit, and a door.

The case 210 forms the appearance of the overall loading part 200. The case 210 may be provided with the tray slot 220, an insertion/retrieval unit 240, the hand unit 250, and a temperature control part therein. An opening may be formed on the side of the case 210 close to the main body 100 of the X-ray irradiation unit 140 so that the tray 1 may be exchanged with the main body 100 of the X-ray irradiation unit 140. The other side of the case 210 may be provided with a door so that the case may be opened and closed, which may allow approach to the inside of the case when the user pulls out the blood bag 2 that has been treated with X-rays or reloads the blood bag 2 that needs X-ray treatment in the loading part 200.

The tray slot 220 is configured to be loaded with a plurality of trays 1. A space of the tray slot 220 may be partitioned by sub-frames 231 and supports 232. A plurality of the tray slots 220 may be provided side by side in the vertical direction on one side in the case 210. Each tray 1 may be configured to be held in one tray slot 220. The tray slot 220 may be formed to be spaced apart from an adjacent tray slot by a predetermined distance so that interference does not occur when the hand unit 250 to be described later picks up the tray 1 and transfers the tray 1. Therefore, the tray slots 220 may be arranged such that, when the trays 1 are loaded in two adjacent tray slots and a hand is inserted between the two trays 1 and grips the lower tray 1, the hand and the upper tray 1 do not interfere with each other.

The tray slot 220 may be connected to and fixed to the sub-frames 231 formed to extend from one point of the case 210 in the vertical direction. The sub-frames 231 are disposed at intervals greater than the width of the tray 1, and may be configured as a pair to serve as a base on which a plurality of supports 232 to be described later may be fixed.

Each tray slot 220 may be provided with a pair of supports 232 spaced apart from each other. The support 232 may be formed to extend in one direction, may support the lower surface of the tray 1, and may be formed in an "L" shape to support the side surface. In this case, a bending direction may be formed in a shape cut in the lateral direction to facilitate insertion of the tray 1 from the side. In the plurality of tray slots 220, the height difference between the respective supports 232 may be determined to be greater than the height of the tray 1 for smooth entry and exit of the tray 1 when the user inserts or reloads the tray 1 in the lateral direction. However, the sub-frames 231 and the plurality of supports 232 constituting the tray slot 220 are only exemplary, and may be modified into various configurations capable of easily exchanging the tray 1 with the outside and loading a plurality of trays.

The insertion/retrieval unit 240 is configured to exchange the tray 1 with the outside. The insertion/retrieval unit 240 may be provided on the upper side of the tray slot 220 and may be configured to move the tray 1 in the horizontal direction. For example, the transfer part 150 may be a conveyor belt that is movable in the horizontal direction. When the hand unit 250 to be described later grips the tray 1 and holds the tray 1 on the upper surface of the insertion/retrieval unit 240, the conveyor is driven to move the tray 1 outside of the loading part 200, then the first position, and next, hand over the tray 1 to the transfer part 150 provided in the main body 100 of the X-ray irradiation unit 140. In addition, the insertion/retrieval unit 240 may take over the tray 1 in which the blood bag 2 that has been treated with X-rays is loaded from the transfer part 150 and move the tray 1 to the inside of the loading part 200. Meanwhile, the insertion/retrieval unit 240 may include a roller which is connected to the drive unit of the insertion/retrieval unit 240 and rotates.

Figure 6A:
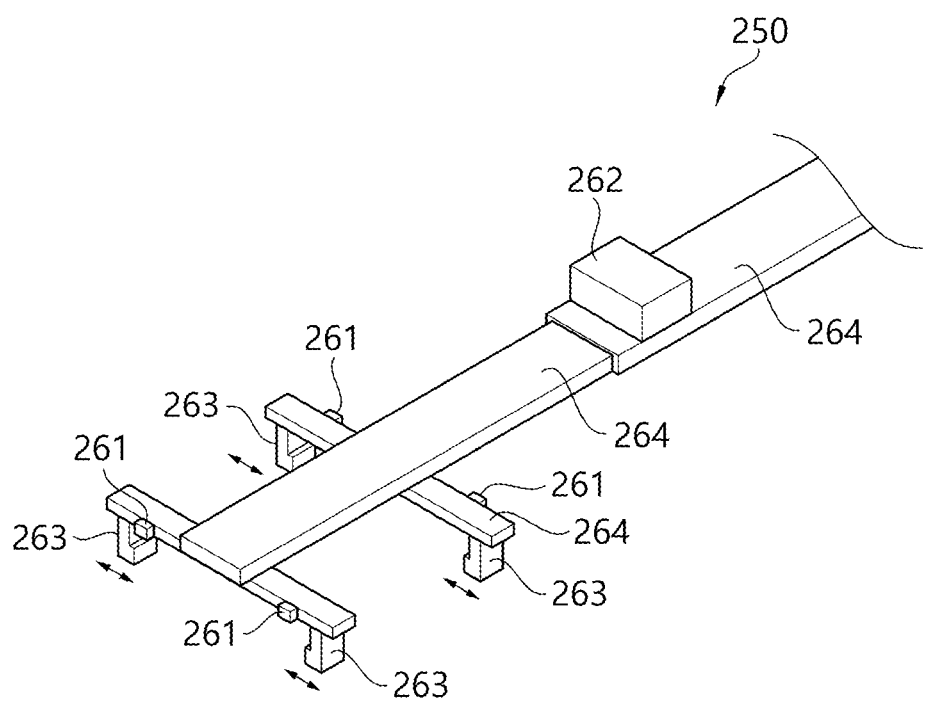
FIG. 6a is a partial perspective view of a hand unit.
Figure 6B:
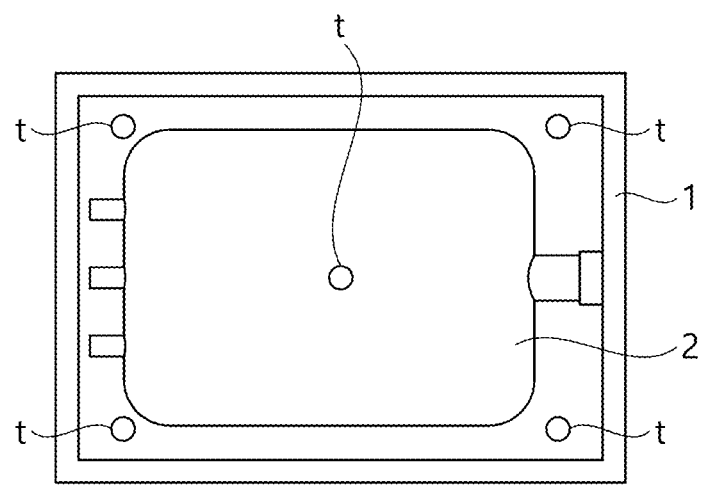
FIG. 6b is a plan view of a tray.

FIG. 6a is a partial perspective view of the hand unit 250, and FIG. 6b is a plan view of the tray 1. Referring to FIG. 6a, the hand unit 250 is configured to transfer the tray 1 inside of the loading part 200. The hand unit 250 is configured to grip the single tray 1 and to perform a main operation between the tray slot 220 and the insertion/retrieval unit 240. The hand unit 250 may be configured to include a plurality of links 264 to enable movement in a first direction for gripping the tray 1, movement in a second direction for removing the tray 1 from the tray slot, and movement in a third direction for moving the tray 1 in the vertical direction. The hand unit 250 may be configured to include at least three drive units to perform the aforementioned movements in the three directions. Each drive unit may be a linear actuator 262 so that movement in a linear direction may be performed. Meanwhile, the hand unit 250 is provided with a pair of gripping units 263 to stably grip the plurality of trays 1, and the gripping units 263 may be configured to be inserted into grooves formed in the tray 1. However, the configuration of the hand and the configuration of the gripping unit 263 corresponding to the tray are only exemplary, and may be modified in various ways capable of stably gripping and transferring the tray 1.

Meanwhile, as shown in FIG. 6b, the hand unit 250 may include sensors configured to determine the location of the blood bag 2 at a plurality of points. A sensor unit 261 may be constituted by distance sensors, for example, and may be configured to individually perform sensing at sensing positions including four regions adjacent to edges and a central portion in the loading space of the blood bag 2 inside the tray. The combination of the measured values makes it possible to check whether the blood bag 2 is loaded and Whether the loading position is defective. The position determination of the blood bag 2 may be made when the hand unit 250 grips the tray 1 for transferring. When the hand unit 250 grips the tray 1, the distance between the sensor unit 261 and the bottom surface of the tray 1 is a constant value, and when the distance is measured shorter than the constant value, a determination may be made that the blood bag 2 is positioned. Meanwhile, with reference to FIG. 9, the position measurement of the blood bag 2 will be described in detail later.

A temperature control unit (not shown) is configured to maintain an appropriate temperature when a plurality of blood bags 2 are loaded. The temperature control unit may be provided on one side of the case 210.

Meanwhile, although not shown, the controller 170 configured to control a driving element inside the loading part 200 may be separately provided. The controller 170 may drive the above-described driving element, drive the hand unit 250 based on values measured from the sensors of the hand unit 250, or transmit a signal to the main body 100 of the X-ray irradiation unit 140.

Figure 7A:
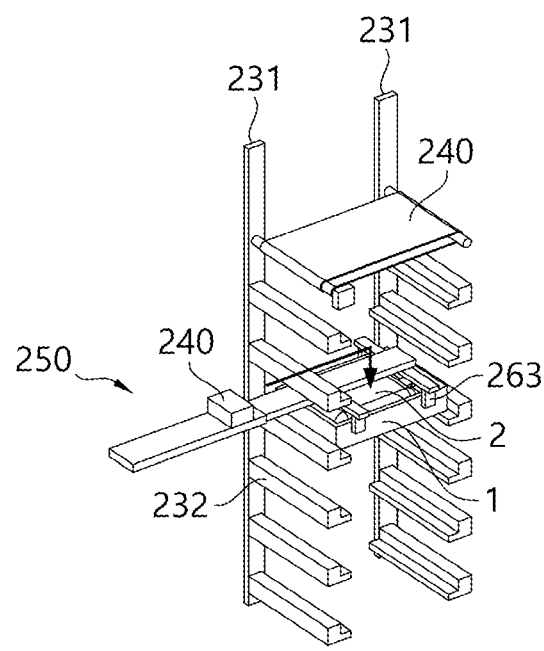
FIGS. 7a, 7b, and 7c are operational state diagrams inside the loading part.
Figure 7B:
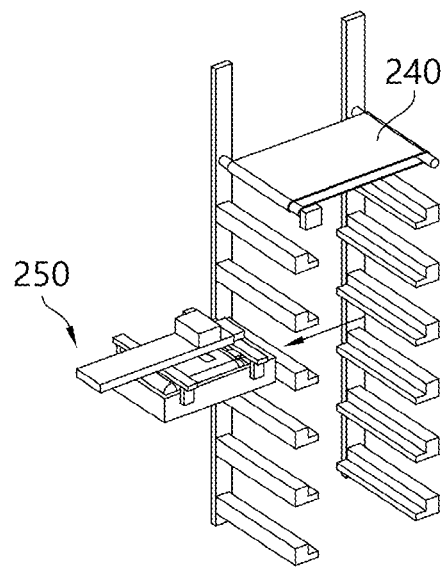
Figure 7C:
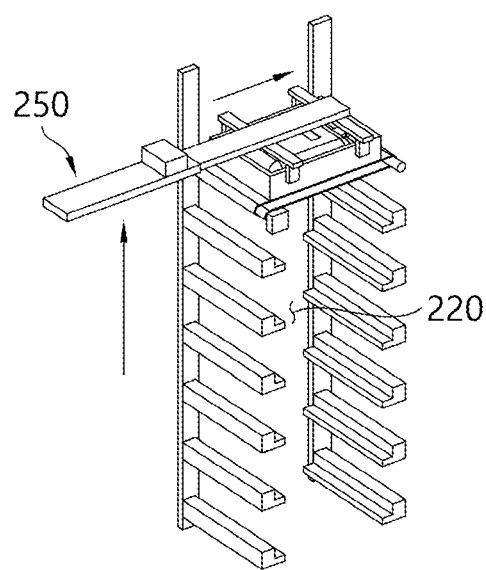

FIGS. 7a, 7b, and 7c are operational state diagrams inside the loading part 200. First, as shown in FIG. 7a, the hand unit 250 moves to the tray slot 220 in which the blood bag 2 that needs X-ray treatment is loaded to grip the tray 1. Then, as shown in FIG. 7b, the hand unit 250 is moved upward by a certain distance in a gripping state to prevent interference with the support 232, and then removes the tray 1 from the slot. Then, the tray 1 is mounted on a seating surface, which is the upper surface of the conveyor of the insertion/retrieval unit 240.

Meanwhile, as shown in FIG. 7c, when the tray 1 in which the blood bag 2 that has been treated with X-rays is loaded is transferred back to the loading part 200, the hand may operate in an order reversed from that described above.

Figure 8A:
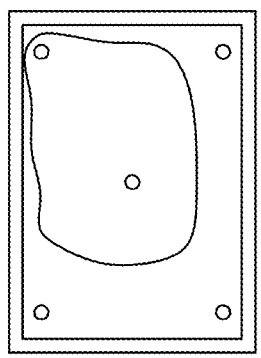
FIGS. 8a, 8b, and 8c are examples of a case where the loading position is defective when the blood bag is loaded on the tray.
Figure 8B:
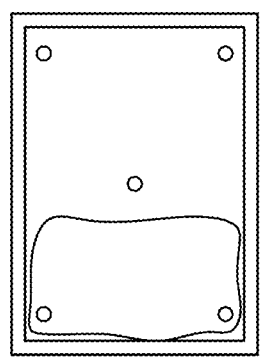
Figure 8C:
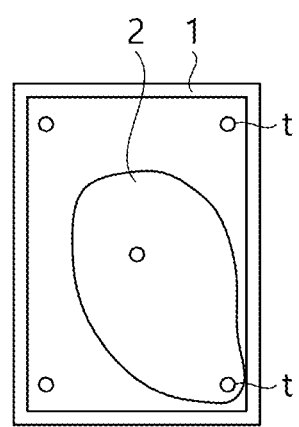

FIGS. 8a, 8b, and 8c are examples of a case where the loading position is defective when the blood bag 2 is loaded on the tray 1. In contrast to the case of FIG. 6b, there may be a case in which the blood bag 2 is detected by one of the sensors at the edges and the sensor at the center (FIGS. 8a and 8c), and a case in which the blood bag 2 is biased to one side and the measurement is performed only with the sensor near the edge (FIG. 8b). In this way, when X-rays are emitted while the blood bag 2 is loaded, there is a concern that the blood bag 2 is partially unevenly subjected to X-ray treatment. In this case, at the time of picking up by the hand unit 250, a case in which the loading position of the blood bag 2 is defective is detected in advance, and the corresponding tray 1 is left as it is without being transferred to the insertion/retrieval unit 240, and the transfer operation of the next tray 1 is performed. At this time, the controller 170 may function to record the loading defect of the corresponding tray 1 and notify the user.

Figure 9:
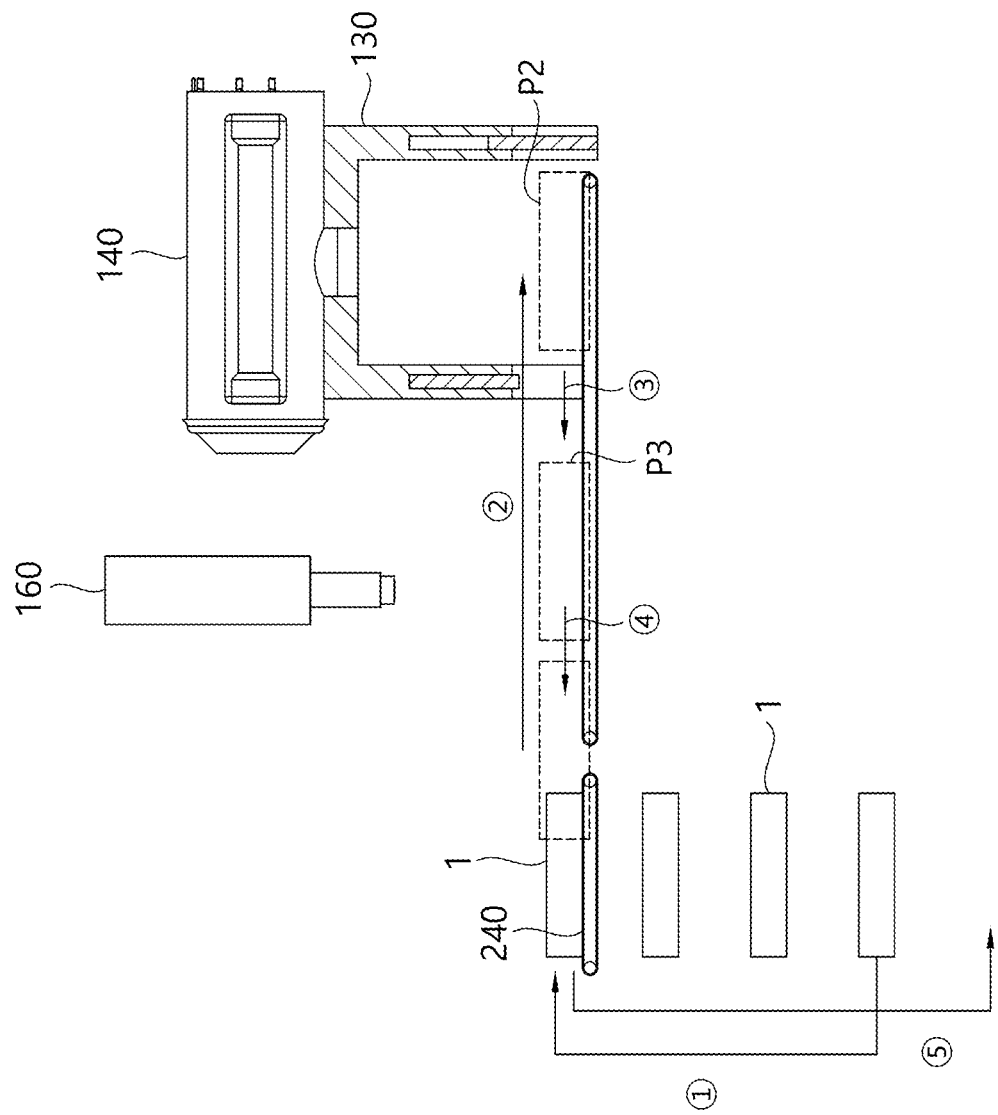
FIG. 9 is a conceptual diagram illustrating a transfer path of the blood bag.

FIG. 9 is a conceptual diagram illustrating a transfer path of the blood bag 2. As shown, the individual blood bag 2 is drawn out from the tray slot 220 in a state of being loaded on the tray 1 and held on the insertion/retrieval unit 240 (①). The insertion/retrieval unit 240 transfers the tray 1 in connection with the transfer part 150, and the transfer part 150 that has taken over the tray 1 transfers the tray 1 into the chamber 130 (②). Then, when the X-ray irradiation is completed, the transfer part 150 transfers the tray 1 in the reverse direction, disposes the tray 1 below the stamping unit 160, performs stamping (③), and then transfers the tray 1 to the insertion/retrieval unit 240 again (④). When the transfer part 150 takes over the tray 1, the hand unit 250 grips the tray 1 to hold the tray 1 in the tray slot 220 where it has been originally positioned (⑤). Then, X-ray irradiation is performed in a unit of single blood bag 2 while changing trays 1. The number of blood bags 2 to be treated with X-rays may be set by the user or may be determined by the number loaded into the loading part 200 by the user.

Hereinafter, another embodiment according to the present disclosure will be described in detail with reference to FIGS. 10 to 12. The present embodiment may be configured to include the same components as those of the above-described embodiment, and descriptions of the same components will be omitted to avoid overlapping descriptions and only the different components will be described in detail.

Figure 10:
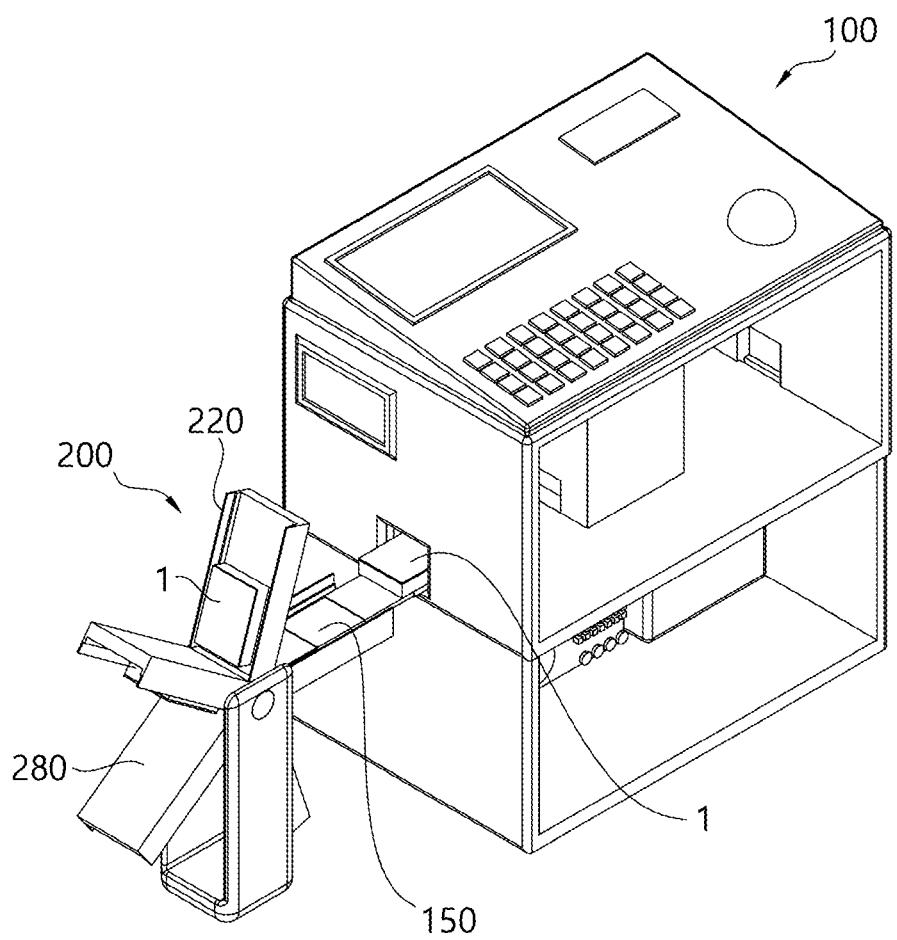
FIG. 10 illustrates an X-ray irradiator for single blood bags according to another embodiment of the present disclosure.
Figure 11:
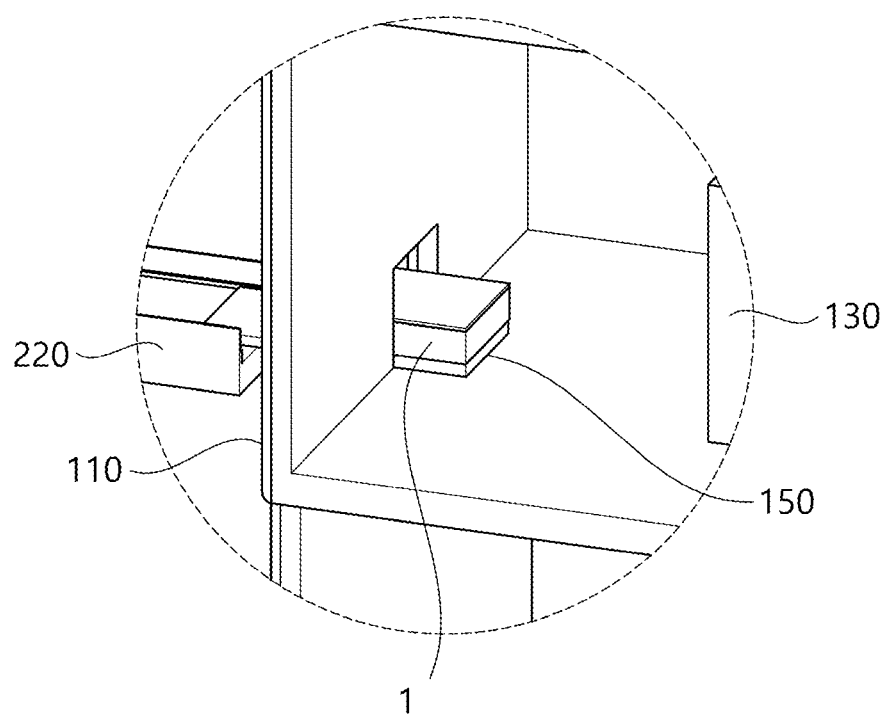
FIG. 11 is an enlarged perspective view of a transfer part of FIG. 10.
Figure 12:
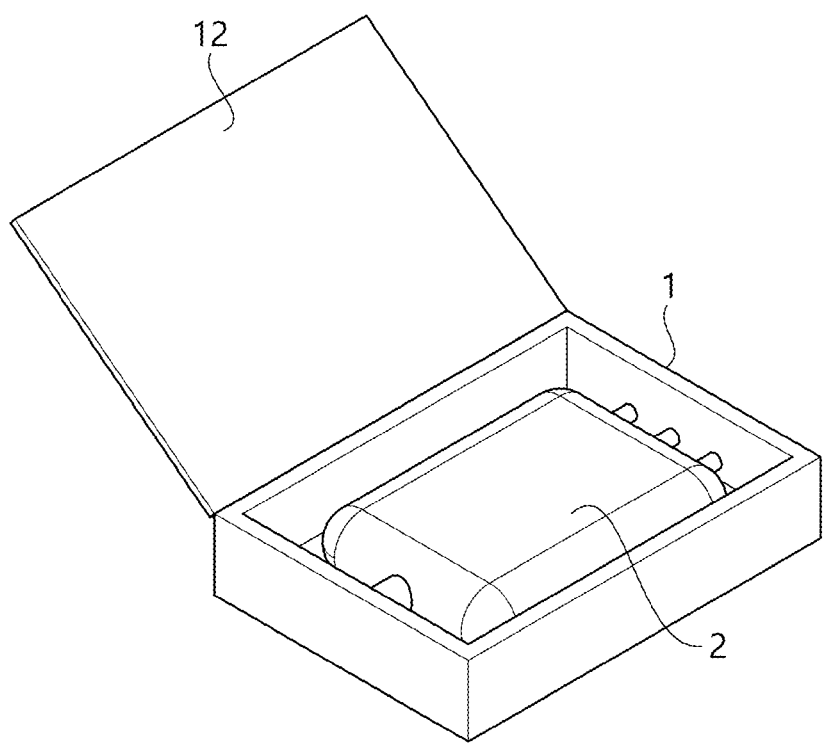
FIG. 12 is a perspective view of a tray of FIG. 10.

FIG. 10 shows an X-ray irradiator for single blood bags 2 according to another embodiment of the present disclosure, FIG. 11 is an enlarged perspective view showing a transfer part 150 of FIG. 10, and FIG. 12 is a perspective view of the tray (1) of FIG. 10.

In a configuration of the loading part 200 shown in FIG. 10, the loading part 200 may be provided with a plurality of tray slots 220 and may be configured to include a rotating frame to be rotatable. The rotating frame 280 may be configured to include a plurality of tray slots 220 formed to be spaced apart from each other at predetermined intervals in a rotation direction, and each tray slot 220 may be configured to extend radially from a rotation center of the rotating frame 280 and be sequentially positioned at a first position P1 during rotation.

However, although not shown, each tray slot 220 may be provided with a holder to prevent displacement during rotation when the tray 1 is loaded. The holder may be connected to a separate drive unit and configured to reciprocate between the fixed position and the release position of the tray 1.

The rotating frame 280 may be configured to minimize the height tolerance with the upper surface of the transfer part 150 of the X-ray irradiation unit 140 for transfer of the tray 1 for smooth movement when exchanging the tray 1 with the X-ray irradiation unit 140.

Referring to FIG. 11, the transfer part 150 of the X-ray irradiation unit 140 may be configured to include a linear actuator (not shown) extending toward the loading part 200 to have an operating range capable of supporting the tray 1 and have an operating range capable of transferring the tray 1 inside the chamber 130 of the main body 100 of the X-ray irradiation unit 140. Here, the transfer part 150 may be configured to have a plurality of layers, and an actuator (not shown) may be provided on each layers to have a large stroke.

Referring to FIG. 12, in the present embodiment, the tray 1 may be provided with a tray door 12 on the upper surface. The tray door 12 is configured to be locked and unlocked relative to the tray 1. Therefore, when the user locks the tray door 12 after loading the blood bag 2 inside the tray 1, it is possible to prevent the driving of the rotating frame 280 from occurring while being loaded on the loading part 200 or to prevent the blood bag 2 from being separated to the outside of the tray 1 when the transfer is made in the main body 100 of the X-ray irradiation unit 140.

As described above, the X-ray irradiator for single blood bags according to the present disclosure may perform X-ray treatment on single blood bags, which may perform an optimized treatment for a small amount of a blood bag, and may simplify a system configuration by using an X-ray tube.

In addition, since a loading part is provided, the number of blood bags desired by a user may be automatically treated with the X-ray, which may have an effect on increasing the degree of freedom of operation.

INDUSTRIAL APPLICABILITY

The present disclosure may be used in medical institutions as an example.

The invention claimed is:

1. An X-ray irradiator for single blood bags, comprising:
    a main body of an X-ray irradiation unit provided with a chamber configured to safely hold a single blood bag therein and an X-ray tube configured to irradiate the chamber with X-rays;
    a loading part configured to load the blood bag; and
    a transfer part configured to transfer the blood bag between the loading part and the chamber to which X-rays are to be emitted,
    wherein the loading part further comprises a hand unit configured to pick up a tray loaded in a tray slot and move the picked up tray to a first position, and
    wherein the hand unit comprises a sensor unit configured to determine a relative position of the blood bag on the tray when the tray is picked up.

2. The X-ray irradiator for single blood bags of claim 1, wherein the tray is configured to load the blood bag.

3. The X-ray irradiator for single blood bags of claim 2, wherein the transfer part is configured to transfer the tray in a state in which the blood bag is held onto the tray.

4. The X-ray irradiator for single blood bags of claim 3, wherein the transfer part is configured to reciprocate the tray between the first position for exchanging the tray with the loading part and a second position for exchanging the tray with the chamber.

5. The X-ray irradiator for single blood bags of claim 4, further comprising a shielding door configured to shield the blood bag from an outside when the blood bag is disposed at an X-ray irradiation position in the chamber.

6. The X-ray irradiator for single blood bags of claim 5, further comprising a stamping unit provided on a reciprocating path of the transfer part, and configured to make a completion mark on the blood bag transferred after X-ray irradiation is completed in the chamber.

7. The X-ray irradiator for single blood bags of claim 6, wherein the stamping unit is provided inside the main body of the X-ray irradiation unit, and is configured to perform stamping by moving downward and contacting an upper surface of the blood bag.

8. The X-ray irradiator for single blood bags of claim 7, wherein the loading part further comprises a housing, and
    wherein the tray slot is provided as a plurality of tray slots inside the housing, and is configured so that a plurality of trays are loaded in a vertical direction, the tray being any one of the plurality of trays.

9. The X-ray irradiator for single blood bags of claim 8, wherein the plurality of tray slots include a plurality of supports spaced apart from each other in the vertical direction to support the plurality of trays, respectively.

10. The X-ray irradiator for single blood bags of claim 1, wherein the hand unit is controlled not to draw the tray out from the tray slot when it is determined that a loading position of the blood bag is defective.

11. The X-ray irradiator for single blood bags of claim 10, wherein the sensor unit of the hand unit comprises a plurality of first sensors provided in regions adjacent to edges of the tray and a second sensor provided in a region adjacent to a central portion in a loading space of the blood bag, and
    wherein the plurality of first sensors and the second sensor are provided facing from top to bottom of the tray and determine a position of the blood bag based on values measured by the plurality of first sensors and the second sensor.

12. The X-ray irradiator for single blood bags of claim 11, further comprising a controller configured to control the main body of the X-ray irradiation unit and the loading part,
    wherein the controller is configured to record data on whether X-ray irradiation is completed on the blood hag loaded in the loading part, or whether the loading position is defective.

13. The X-ray irradiator for single blood bags of claim 7, wherein the tray slot is provided as a plurality of tray slots formed to extend radially, and
    wherein the loading part further comprises a rotating frame, the rotating frame is configured to be rotated and comprises the plurality of tray slots, and the rotating frame is further configured to locate each of the tray slots to the first position as the rotating frame is rotated.

14. The X-ray irradiator for single blood bags of claim 13, wherein a plurality of trays that include the tray are loaded in the plurality of tray slots, and each of the plurality of tray slots further comprises a holder configured to prevent a corresponding one of the plurality of trays loaded therein from being separated.

15. The X-ray irradiator for single blood bags of claim 13, wherein the tray further comprises a tray door configured to prevent the blood bag from being separate.

* * * * *